(12) United States Patent
Luo et al.

(10) Patent No.: US 9,039,616 B2
(45) Date of Patent: May 26, 2015

(54) ULTRASONIC BONE ASSESSMENT APPARATUS WITH ADJUSTABLE ULNA STYLOID SUPPORT AND METHOD

(75) Inventors: Gangming Luo, Elmhurst, NY (US); Jonathan J. Kaufman, Brooklyn, NY (US)

(73) Assignee: CyberLogic, Inc., New York City, NY (US)

( * ) Notice: Subject to any disclaimer, the term of this patent is extended or adjusted under 35 U.S.C. 154(b) by 257 days.

(21) Appl. No.: 13/201,156

(22) PCT Filed: Feb. 11, 2010

(86) PCT No.: PCT/US2010/023861
§ 371 (c)(1),
(2), (4) Date: Aug. 11, 2011

(87) PCT Pub. No.: WO2010/093769
PCT Pub. Date: Aug. 19, 2010

(65) Prior Publication Data
US 2011/0313289 A1    Dec. 22, 2011

Related U.S. Application Data

(60) Provisional application No. 61/207,716, filed on Feb. 13, 2009.

(51) Int. Cl.
*A61B 5/103* (2006.01)
*A61B 8/08* (2006.01)
*A61B 5/00* (2006.01)
*A61B 6/00* (2006.01)
*A61B 8/00* (2006.01)

(52) U.S. Cl.
CPC .............. *A61B 8/0875* (2013.01); *A61B 5/0055* (2013.01); *A61B 6/00* (2013.01); *A61B 5/00* (2013.01); *A61B 8/4209* (2013.01)

(58) Field of Classification Search
CPC ............................ A61B 8/0875; A61B 8/4209
USPC ........................................................... 600/437
See application file for complete search history.

(56) References Cited

U.S. PATENT DOCUMENTS

| 2005/0004457 A1* | 1/2005 | Moilanen et al. ............. 600/437 |
| 2008/0146927 A1 | 6/2008 | Luo et al. |

FOREIGN PATENT DOCUMENTS

| JP | 2000005171 | 1/2000 |
| JP | 2001061837 | 3/2001 |

OTHER PUBLICATIONS

International Search Report issued in International (PCT) Patent Application No. PCT/US2010/023861 (Dec. 8, 2010).

(Continued)

*Primary Examiner* — Unsu Jung
*Assistant Examiner* — Serkan Akar
(74) *Attorney, Agent, or Firm* — Reising Ethington P.C.

(57) ABSTRACT

An invention is disclosed for locating a region of interest (ROI) in the radius. A method and apparatus are disclosed that use a pair of ultrasound transducers for ultrasound assessment of various properties of bone. The invention includes positioning the transducers on the anterior-posterior (dorsal and ventral) sides of a forearm of an individual. The positioning is based on the forearm length, and a selected percentage of this length at which the ROI is desired. In a presently preferred embodiment of the invention, the ROI is defined as the $\frac{1}{3}^{rd}$ location. An arm is placed in an ultrasound fixture which has a first surface, a second surface with a raised portion against which the ulna styloid process is placed, and a third surface on which the elbow is placed. The distance between the raised portion of the second surface and the centerlines of the pair of ultrasound transducers is adjustable. The positioning so obtained leads to the ability to make both (i) reproducible measurements and (ii) to be able to compare the results obtained in one person with another, because relatively analogous portions of the radii are assessed in both. In an alternative embodiment of the invention, a single transducer is positioned similarly on the forearm, operating in pulse-echo mode.

16 Claims, 2 Drawing Sheets

(56) References Cited

OTHER PUBLICATIONS

Written Opinion issued in International (PCT) Patent Application No. PCT/US2010/023861 (Dec. 8, 2010).

International Preliminary Report on Patentability issued in International (PCT) Patent Application No. PCT/US/2010/023861 (Aug. 25, 2011).

* cited by examiner

ULTRASONIC BONE ASSESSMENT APPARATUS WITH ADJUSTABLE ULNA STYLOID SUPPORT AND METHOD

RELATED U.S. APPLICATION

This application is the national stage application of, and claims priority to, International Application No. PCT/US2010/023861 filed Feb. 11, 2010, the entire disclosure of which is incorporated herein by reference. The International Application was published in the English language on Aug. 19, 2010 as International Publication No. WO 2010/093769 and itself claims the benefit of U.S. Provisional Patent Application No. 61/207,716 filed Feb. 13, 2009, the entire disclosure of which is incorporated herein by reference.

FIELD OF THE INVENTION

The present invention relates generally to apparatus and method for non-invasively and quantitatively evaluating bone tissue in vivo. More specifically, the invention pertains to osteoporosis diagnosis, bone fracture risk assessment, and bone fracture diagnosis using an ultrasound apparatus and method. Even more specifically, the invention relates to a method and apparatus for locating a region of interest within a radius that allows for both reproducible and comparative measurements of a set of ultrasound parameters associated with a given subject or set of subjects.

BACKGROUND OF THE INVENTION

In recent years, ultrasound has received a great deal of attention as a new technique for noninvasive assessment of bone, and numerous attempts have been made to use ultrasound energy for evaluating the condition of bone tissue in vivo, and thus for determining a measure of osteoporosis and assessing bone fracture risk.

In particular, Hoop discloses in U.S. Pat. No. 3,847,141 a device to measure bone density as a means for monitoring calcium content of the involved bone. A pair of opposed ultrasonic transducers is applied to opposite sides of a subject's finger, such that recurrent pulses transmitted via one transducer are 'focused" on the bone, while the receiver response of the other transducer is similarly "focused" to receive pulses that have been transmitted through the bone. The circuitry in Hoop is arranged such that filtered reception of one pulse triggers the next pulse transmission; the filtering is by way of a bandpass filter, passing components of received signals in the 25 kHz to 125 kHz range only; and the observed frequency of retriggering is believed to be proportional to the calcium content of the bone. Thus Hoop is concerned only with what he defines to be transit time for pulses in the indicated band.

Pratt, Jr. deals with establishing, in vivo, the strength of bone in a live being such as a horse. In U.S. Pat. No. 4,361,154, the inventor solves the problem posed by measuring transit time from "launch" to "reception" of pulses of 0.5 MHz and 1.0 MHz through the bone and soft tissue, and from measurement of pulse-echo time, to thereby derive a measurement of transit time through bone alone. A data bank enables the evaluation of the bone condition from the measured transit times. U.S. Pat. No. 4,913,157, also granted to Pratt, Jr., operates on the same general principle of transit time/velocity deduction, using the latter preferred frequency of 2.25 MHz as the base frequency of pulsed "launchings" and a technique of matched filtering/Fourier transform filtering for further analyzing received pulses.

Palmer et al. disclose in U.S. Pat. No. 4,774,959 a bone measurement system deriving the slope of the relation between ultrasonic frequency and attenuation of a sequence of tone signals. Being in the range of 200 kHz to 600 kHz, the signals are applied to one transducer and received by another transducer. The passage of the signals between the two transducers with and without the intervening presence of a heel bone is compared, with the assumption that the frequency/attenuation relation is a straight line, i.e., of constant slope.

U.S. Pat. No. 4,926,870 granted to Brandenburger discloses another in vivo bone analysis system which depends upon measuring transit time for an ultrasonic signal along a desired path through bone. A "canonical" waveform, determined by previous experience to be on the correct path, is used for comparison against received signals for transmission through the patient's bone, while the latter is reoriented until the received signal indicates that the bone is aligned with the desired path. Again, ultrasonic velocity through the patient's bone is assumed to have been determined from measured transit time.

Rossman et al. disclose in U.S. Pat. No. 5,054,490 an ultrasound densitometer for measuring physical properties and integrity of bone, upon determination of a transit time through bone. Alternatively, the Rossman et al. device compares absolute attenuation of specific frequency components of ultrasound signals through the bone with the absolute attenuation of the same frequency components through a medium of known acoustic properties.

Mele et al., disclose in U.S. Pat. No. 5,564,423, and in a subsequent related Patent by Cadossi et al. (U.S. Pat. No. 6,436,042), disclose a device that measures the "amplitude dependent speed of sound" through a bony member in a living body. The method relies on the visual display of the received ultrasound signal, and the selection of a specific portion of the waveform for analysis.

Significant steps in advancing ultrasound bone assessment have been made by Kaufman et al. (in U.S. Pat. Nos. 5,259,384 and 5,651,363) and by Chiabrera et al. (in U.S. Pat. Nos. 5,785,656 and 5,879,301). In these Patents, an estimate of a "bone transfer function" associated with a given bone is obtained in a statistically optimal fashion, and parametric estimates of the phase and attenuation functions associated with it are determined. The disclosed methods also describe the use of 2D array transducers for obtaining more reproducible estimates of the bone density, architecture, and fracture risk.

Notwithstanding the advances made in the past in previous attempts, as exemplified by the above-mentioned apparatuses and methods, there are still additional improvements needed in order to make ultrasound assessment a widely used technique for accurately and precisely assessing the bone density, architecture, quality, fracture diagnosis, and fracture risk of a subject.

SUMMARY OF THE INVENTION

It is accordingly a primary object of this invention to provide an improved method and apparatus for characterizing and determining non-invasively the properties of bone. A more particular though not limiting object of the invention is to provide a method and apparatus for non-invasive and quantitative evaluation of bone tissue in vivo, to make accurate and precise osteoporosis diagnosis and monitoring possible.

Another object is to meet the above objects in such a way that the bone tissue evaluation and the osteoporosis diagnosis may be performed in a much more convenient and reliable manner than those previously used.

A further object is to meet the above object in such a way that the bone tissue evaluation and the osteoporosis diagnosis may be performed with relatively more simple and inexpensive means than those previously used.

A still further object is to locate a region of interest of the radius that is clinically relevant to assessment of osteoporosis, adjusts to the length of the radius thereby maintaining the same relative region of interest across subjects, and at the same time maintains excellent reproducibility.

As compared with the prior art, the invention utilizes a novel method for reliably and reproducibly locating a region of interest (ROI) in a given subject in order to assist in achieving the indicated objectives. In particular, in the present invention a pair of ultrasound transducers are located a given distance from the end of the ulna that is proportional to the length of the forearm.

Accordingly, the present invention utilizes a new configuration to identify a ROI of a radius of a living being, to more conveniently, accurately and precisely determine the characteristics of the radius—to thereby determine one or more of the bone properties such as fracture risk, strength, density, bone mineral density, bone mineral content, quality, cortical thickness, cortical cross-sectional area, bone width and/or architecture of the bone. The advantage of such an approach is its inherent simplicity and convenience, as well as its increased sensitivity to the underlying state of the interrogated bone. This is in contrast to the prior art which can not extract as much information on the underlying bone in such a convenient, reproducible and effective manner.

The invention in its presently preferred form of a method and apparatus of locating and identifying a region of interest of a radius, achieves the foregoing objectives by reproducibly placing a pair of collinearly-aligned ultrasound transducers according to a size associated with a given subject. In the presently preferred embodiment of the invention, the size is the length of the forearm, that is, the distance from the distal end of the ulna styloid (styloid process) to the elbow (olecranon). In the presently preferred embodiment of the invention, the forearm length is separately measured with a ruler.

In an attempt to develop a simple apparatus and method for ultrasonically assessing a radius, that offers both good reproducibility and measures relatively the same region of interest among a set of individuals, the present inventors have recognized that along the radius there is considerable variation in bone quantities (e.g., bone mineral density and cortical thickness vary significantly along the length of the radius bone). In addition, x-ray bone densitometers have used various regions of interest (ROI) to assess the forearm, one of the most common being the $\frac{1}{3}^{rd}$ location (see for example the book "Bone Densitometry in Clinical Practice", $2^{nd}$ Edition, by Sydney Lou Bonnick, and published by Humana Press in Totowa, N.J. in 2004, the entire reference of which is incorporated by reference hereinto). These ROI are in the x-ray case identified through the image produced in the process of acquiring the bone density data. Such an approach is not possible in ultrasound bone assessment. In addition, manual placement of an arm into an ultrasound fixture is subject to technician error and thus may lead to relatively poor reproducibility as well as to the inability to compare different subjects with one another because of the variation of the radius properties along the length of the bone.

DETAILED DESCRIPTION OF EMBODIMENTS OF THE INVENTION

Figure 1:
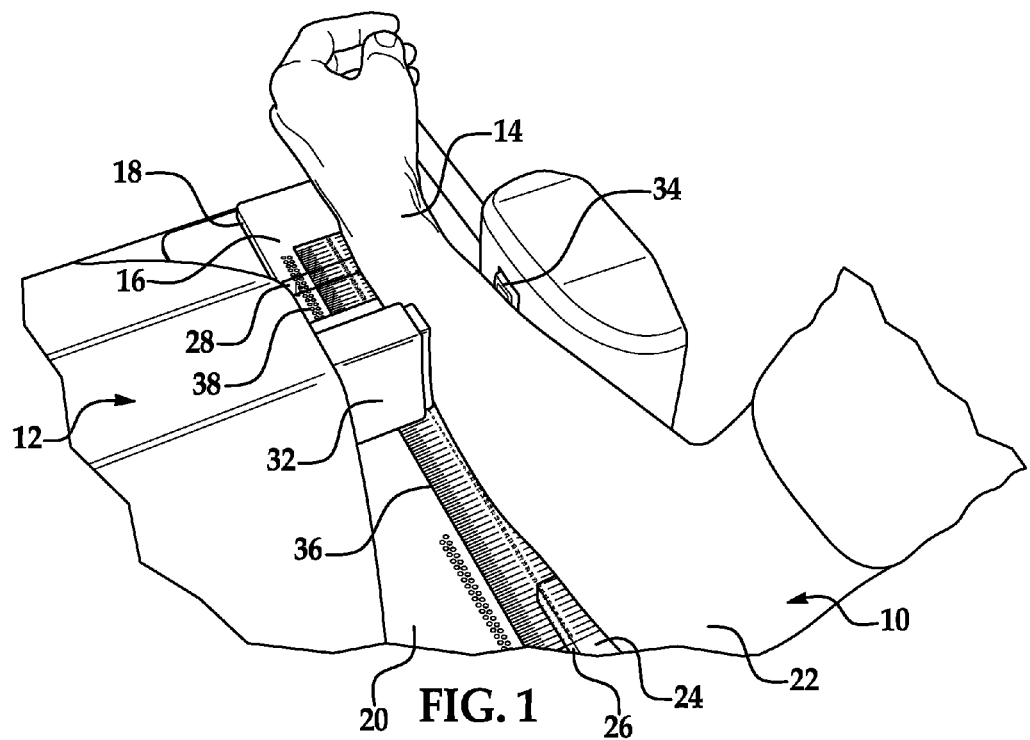
FIG. 1 is a picture showing the main components of an apparatus of the invention that is used to locate a region of interest of a radius in a living being. As may be seen, the forearm is pressed between two transducers at the $\frac{1}{3}^{rd}$ location, the elbow rests on a block (surface), the wrist rests on a block (another surface) with a support element or raised portion, and the two surfaces rest on another surface, onto which a scale is attached.
Figure 2:
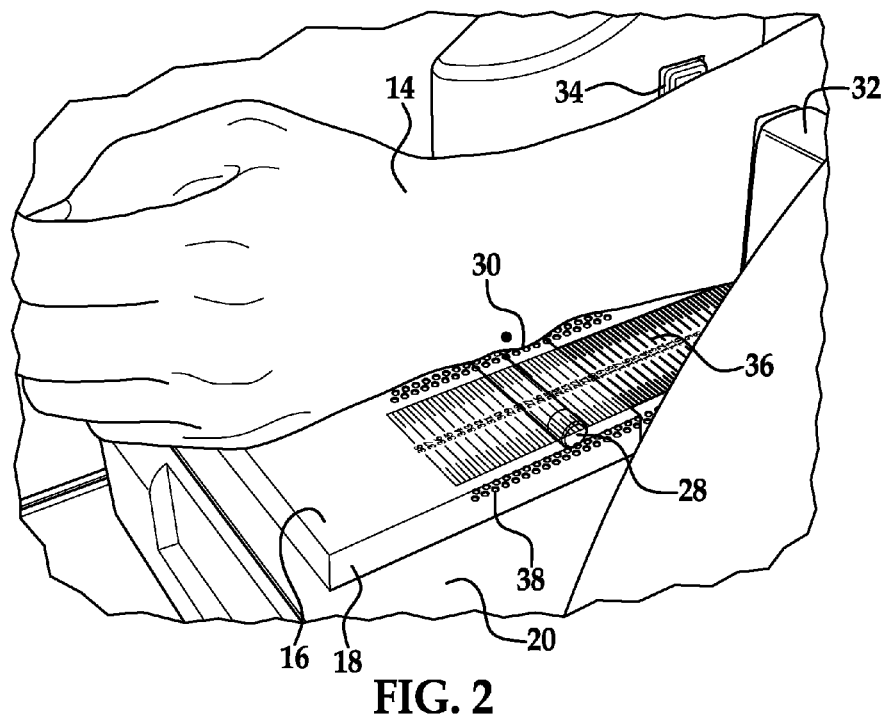
FIG. 2 shows a close view of the positioning apparatus. A dot has been placed on the skin overlying the distal side of the ulna styloid, as an aid for the technician to place the forearm in the proper position.
Figure 3:
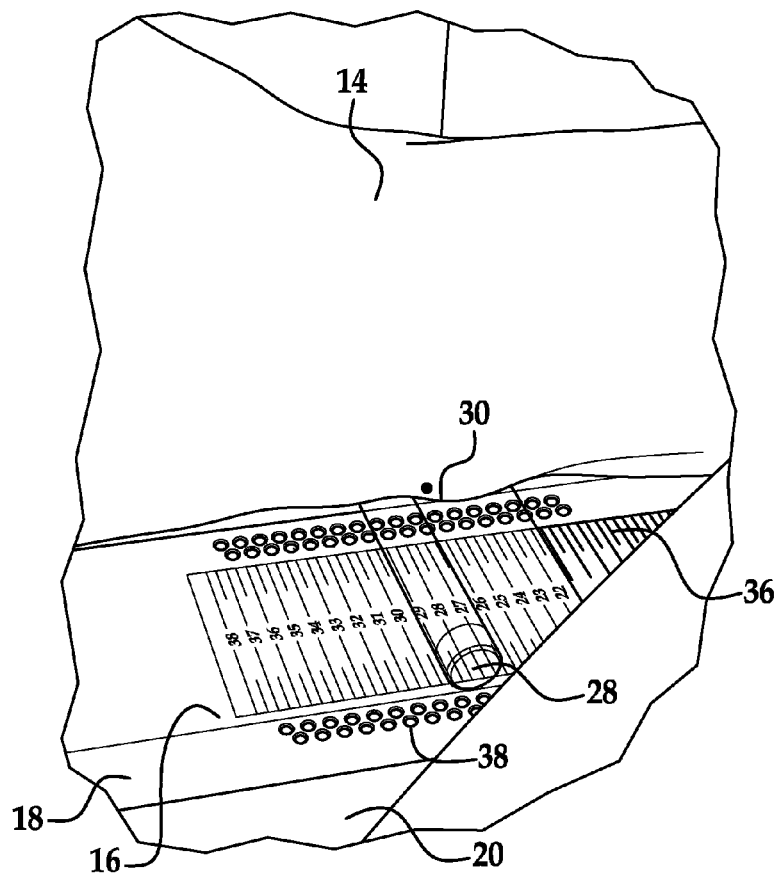
FIG. 3 shows another closer view of the positioning apparatus. In the presently preferred embodiment of the invention, a unit one on the scale is equal to $\frac{1}{3}$ cm, leading to a measurement site at the $\frac{1}{3}^{rd}$ location, when the block (surface) with the support element or raised portion is placed in the correct position (i.e., in the case of an individual having a forearm length of 27 cm, the correct location is such that the near surface of the plastic rod is set to be located at "27 units" on the scale, or 9 cm in actuality from the centerline of the transducers).
Figure 4:
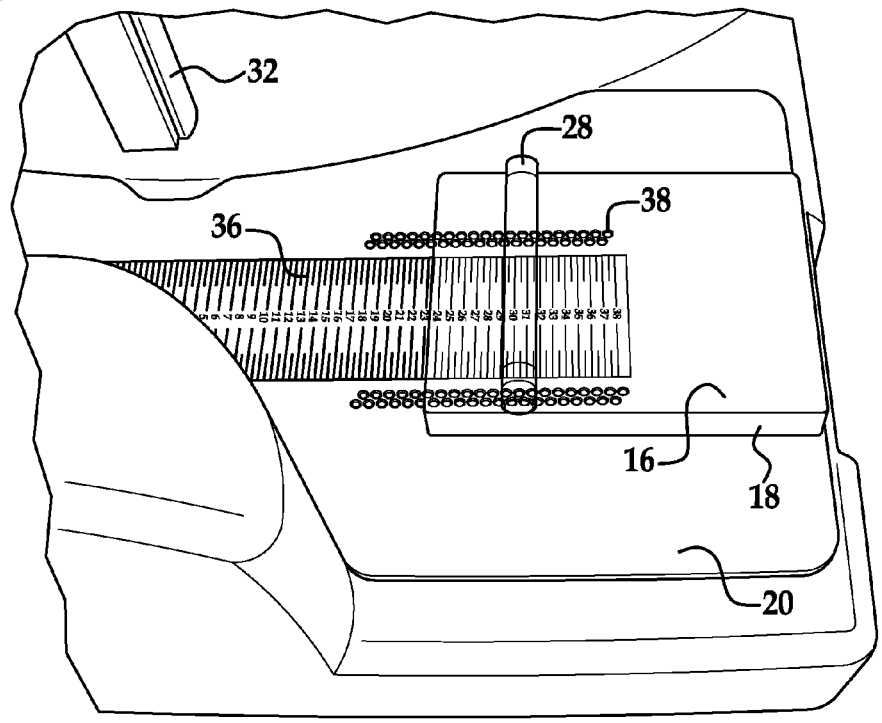
FIG. 4 shows an image of a portion of the positioning apparatus. It should be understood that in this embodiment of the invention pins located under the block with the support element or raised portion (i.e., the rod) are used to position the block in the correct location, using the associated set of holes.

In the presently preferred embodiment of the invention, and with additional reference to FIGS. 1-4, an arm 10 is placed into an ultrasound device 12. The wrist 14 is placed on a surface 16 of a block 18 that rests on a surface 20, while the elbow 22 rests on a surface 24 of a block 26 that itself rests on the surface 20. In the illustrated embodiment, blocks 18, 26 are made from a transparent material. The surface 16, as may be seen, has a support element in the form of a raised portion 28 in the illustrated embodiment (which is also transparent in the illustrated embodiment); in the presently preferred embodiment of the invention, the raised portion 28 is a $\frac{5}{16}"$ diameter plastic rod. The arm 10 is placed in such a way so that the ulna styloid 30 (the "bump" at the distal end of the bone near the wrist 14) is placed firmly against the raised portion 28. With the elbow (olecranon) 22 placed on the surface 24, the transducers 32, 34 are closed onto the arm 10 to enable acoustic transmission of the ultrasound wave from one transducer to the other (it should be understood that acoustic coupling fluid or gel will generally be used to ensure efficient coupling of the ultrasound signal.) The apparatus and method so disclosed enables the positioning of the transducers 32, 34 both reproducibly and to measure the same relative portion of the radius among a group of individuals. In the presently preferred embodiment of the invention the surface 16 with the raised portion 28 against which the distal side of the ulna styloid 30 rests is movable to account for both varying arm lengths (i.e., forearms) and the percentage of forearm length where the ROI is to be located. In the presently preferred embodiment of the invention, the $\frac{1}{3}^{rd}$ location is used to site the ultrasound measurement. As an example, for a forearm length of 27 cm, the $\frac{1}{3}^{rd}$ location means that the center lines (the lines that divide the transducer faces in half along the longer dimension) of the transducer faces are to be located 9 cm from the distal end of the ulna styloid 30, that is, 9 cm from the raised portion 28 of the surface 16. In the presently preferred embodiment of the invention, for a 27 cm forearm length, the near surface of the $\frac{5}{16}"$ diameter rod (that is the near surface of the raised portion 28 of the surface 16) would be positioned so that it is 9 cm from the center of the transducers 32, 34. In the presently preferred embodiment of the invention, a scale 36 is attached to the surface 20; a unit of 1 on the scale 36 is equal to ⅓ cm; this enables a technician to measure the length of the forearm and not to have to divide by three. Therefore, for a forearm length of 27 cm, the technician places the surface 16 with the raised portion 28 at the "unit 27" location on the scale 36 which provides for a distance of 9 cm from the center of the transducers 32, 34 to the distal side of the ulna styloid 30. In the presently preferred embodiment of the invention, holes 38 are spaced ⅙ cm (1.67 mm), and a pair of pins (not shown) on the bottom of the piece which has the raised portion 28 are placed into the holes 38 corresponding to a given forearm length, using the scale 36 as a guide to locate the correct holes 38. It should be appreciated that a forearm length is necessary to be made separately in order to use the invention in its presently preferred form. It should be further appreciated that although the invention as disclosed utilizes two ultrasound transducers 32, 34, an embodiment with only one transducer (for pulse-echo operation) should also be considered to be within the scope of the present invention.

It should be further appreciated that the disclosed techniques can work with any number of ultrasound signal processing methods and parameters. Therefore, it should be appreciated that any set of ultrasound parameters may be utilized in conjunction with the methods and apparatuses of the present invention. In particular, the methods and apparatuses as disclosed in U.S. Pat. Nos. 5,259,384, 5,651,363, 5,785,656 and 5,879,301, as well as in U.S. Patent Application Nos. 20080194952 and 20050197576, all of which are incorporated by reference hereinto, and should be understood to be applicable to the present invention.

In the presently preferred embodiments of the invention, the forearm is not in contact with the lowest surface 20 of the apparatus, near the ROI location, i.e., near where the transducers 32, 34 are in contact with the skin. This has been found to improve the accuracy and precision of the ultrasound data and bone property estimates. However, it should be understood that the invention can in certain embodiments allow direct skin contact near the transducers 32, 34. Thus in another embodiment of the invention, only the lowest surface 20 is used, and the raised portion 28 (in this case a semicircular rod) is attached to the lowest surface 20, and the elbow 22 rests on the lowest surface 20 itself. It should also be appreciated that the scale 36 can be etched directly into the lowest surface 20, and the raised portion 28 can be positioned (according to arm length) using a variety of techniques, not just pins and holes 36. For example, a slide mechanism can be used. This can be particularly useful when only the lowest surface 20 is used (and not the blocks 18, 26 defining the other two surfaces 16, 24). It should also be understood that a variety of shapes can be used for the raised portion 28 of the apparatus (with or without block 18 and surface 16). Besides the cylindrical rod and semi-circular rod as already disclosed hereinabove, other shapes more adapted to the shape of distal end of the ulna styloid 30 can also be utilized.

It should be understood that the methods and apparatuses disclosed herein for locating a region of interest of a radius within a forearm of a subject can be utilized not only with ultrasound but with other types of wave generators as well, such as for x-ray bone densitometry. (In this latter case, an image of the bone would not have to be generated to locate the ROI.)

It should be further appreciated that the invention should also be understood to encompass not only positioning based on use of the ulna styloid 30, but other landmarks could be utilized as well, for example the length of the arm from elbow 22 to the center of the hand clenched into a fist.

It should be further understood that the present invention can be used for locating a region-of-interest not only at the ⅓$^{rd}$ location, but for any portion of the radius. In another presently preferred embodiment of the invention, the eight (8) percent location is utilized; this corresponds to a significant amount of trabecular bone (in addition to the cortical portion) and can find use in assessing bone loss in osteoporosis. It should be further appreciated that the methods as disclosed herein can be used to locate a region-of-interest on not only the radius, but the ulna as well.

The invention as described herein achieves the primary objectives of the inventors, namely to locate a region of interest that is clinically relevant to assessment of osteoporosis, adjusts to the size of the radius thereby maintaining the same relative region of interest across subjects, and at the same time maintains excellent reproducibility. While several embodiments of the present invention have been disclosed hereinabove, it is to be understood that these embodiments are given by example only and not in a limiting sense. Those skilled in the art may make various modifications and additions to the preferred embodiments chosen to illustrate the invention without departing from the spirit and scope of the present contribution to the art. Accordingly, it is to be realized that the patent protection sought and to be afforded hereby shall be deemed to extend to the subject matter claimed and all equivalence thereof fairly within the scope of the invention.

We claim:

1. An apparatus for aligning a wave generator with a region of interest in a bone within an arm of a subject, comprising:
   said wave generator comprising one of a first ultrasound transducer and an x-ray machine;
   a first surface configured to support a forearm of said arm in a defined position relative to said wave generator;
   a support element disposed on said first surface and configured to be positioned under a wrist of said arm in alignment with an ulna styloid of said forearm, said support element spaced from said wave generator in a longitudinal direction of said forearm
   wherein said support element is movable relative to said wave generator in the longitudinal direction of said forearm to vary a distance between said support element and said wave generator in the longitudinal direction of said forearm and thereby align said wave generator with said region of interest, said distance determined responsive to a measurement associated with said arm.

2. The apparatus of claim 1, further comprising a second ultrasound transducer disposed on an opposite side of said arm relative to said first ultrasound transducer.

3. The apparatus of claim 1 wherein said support element comprises a cylindrical rod.

4. The apparatus of claim 1 wherein said first surface includes a scale.

5. The apparatus of claim 1 wherein the measurement comprises a distance from a distal end of said ulna styloid of the arm to an elbow of the arm.

6. The apparatus of claim 4 wherein each unit on said scale corresponds to one third of a measurement unit of the measurement.

7. An apparatus for aligning a wave generator with a region of interest in a bone within an arm of a subject, comprising:
   said wave generator;
   a first surface configured to support a forearm of said arm in a defined position relative to said wave generator;

a first block disposed on top of said first surface, said first block defining a second surface spaced from and parallel to said first surface and configured to support a wrist of said arm;

a support element disposed on said first block and configured to be positioned under a wrist of said arm in alignment with an ulna styloid of said forearm, said support element spaced from said wave generator in a longitudinal direction of said forearm; and, a second block disposed on top of said first surface and spaced from said first block, said second block defining a third surface spaced from and parallel to said first and second surfaces and configured to support an elbow of said arm, said wave generator disposed between said first and second blocks;

wherein said first block and said support element are movable relative to said wave generator in the longitudinal direction of said forearm to vary a distance between said support element and said wave generator in the longitudinal direction of said forearm and thereby align said wave generator with said region of interest, said distance determined responsive to a measurement associated with said arm.

8. The apparatus of claim 7, wherein said first surface includes a scale, at least a portion of said scale is disposed underneath said first block and said first block is made from a transparent material.

9. The apparatus of claim 8 wherein each unit on said scale corresponds to one third of a measurement unit of the measurement.

10. A method for aligning a wave generator with a region of interest in a bone within an arm of a subject, comprising the steps of:

providing said wave generator comprising one of a first ultrasound transducer and an x-ray machine and a first surface configured to support a forearm of said arm in a defined position relative to said wave generator, said first surface including a support element disposed thereon and configured to be positioned under a wrist of said arm in alignment with an ulna styloid of said forearm, said support element spaced from said wave generator in a longitudinal direction of said forearm; and, moving said support element relative to said wave generator in the longitudinal direction of said forearm to vary a distance between said support element and the wave generator in the longitudinal direction of said forearm and thereby align said wave generator with said region of interest, said distance determined responsive to a measurement associated with said arm.

11. The method of claim 10, wherein a second ultrasound transducer is disposed on an opposite side of said arm relative to said first ultrasound transducer.

12. The method of claim 10, further comprising the steps of:

positioning a wrist of said arm on a second surface defined by a first block disposed on top of said first surface, said second surface spaced from and parallel to said first surface and said support element disposed on said first block; and, positioning an elbow of said arm on a third surface defined by a second block disposed on top of said first surface and spaced from said first block, said third surface spaced from and parallel to said first and second surfaces and said wave generator disposed between said first and second blocks.

13. The method of claim 10 wherein said support element comprises a cylindrical rod.

14. The method of claim 10 wherein said first surface includes a scale.

15. The method of claim 10, further comprising the step of positioning said arm such that said support element supports said ulna styloid.

16. An apparatus for aligning a wave generator with a region of interest in a bone within an arm of a subject, comprising:

said wave generator;

a first surface configured to support a forearm of said arm in a defined position relative to said wave generator;

first and second blocks disposed on top of said first surface, said first and second blocks spaced from one another in the longitudinal direction of said forearm and disposed on opposite sides of said wave generator, said first block configured to support a wrist of said arm and said second block configured to support an elbow of said arm;

a support element disposed on said first block and configured to be positioned under a wrist of said arm in alignment with an ulna styloid of said forearm, wherein said first block and said support element are movable relative to said wave generator in the longitudinal direction of said forearm to vary a distance between said support element and said wave generator in the longitudinal direction of said forearm and thereby align said wave generator with said region of interest, said distance determined responsive to a measurement associated with said arm.

* * * * *